United States Patent
Baek et al.

(10) Patent No.: US 12,383,479 B2
(45) Date of Patent: Aug. 12, 2025

(54) COSMETIC COMPOSITION COMPRISING PALMITOYLETHANOLAMIDE FOR SOOTHING EFFECT ON THE SKIN

(71) Applicant: LG HOUSEHOLD & HEALTH CARE LTD., Seoul (KR)

(72) Inventors: Ji Hae Baek, Seoul (KR); Moon Ju Kim, Seoul (KR); Oh Sun Kwon, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 178 days.

(21) Appl. No.: 18/085,752

(22) Filed: Dec. 21, 2022

(65) Prior Publication Data

US 2023/0190600 A1   Jun. 22, 2023

(30) Foreign Application Priority Data

Dec. 22, 2021   (KR) .................. 10-2021-0185262

(51) Int. Cl.
 *A61K 8/34* (2006.01)
 *A61K 8/42* (2006.01)
 *A61Q 19/00* (2006.01)

(52) U.S. Cl.
 CPC ............ *A61K 8/345* (2013.01); *A61K 8/42* (2013.01); *A61Q 19/00* (2013.01); *A61K 2800/49* (2013.01)

(58) Field of Classification Search
 CPC ............ A61K 8/345; A61K 9/0014; A61K 2800/5922; A61K 8/42; A61K 2800/10; A61K 8/922; A61K 8/042; A61K 2300/00; A61K 8/0212; A61K 47/18; A61K 9/282; A61K 9/2013; A61Q 19/00; A61Q 19/08; A61Q 17/04; A61Q 19/10; A61Q 19/007; A61Q 19/005; A61Q 19/008; A61Q 1/00; A61Q 1/08
 See application file for complete search history.

(56) References Cited

U.S. PATENT DOCUMENTS

2002/0182159 A1   12/2002   McGlone et al.
2013/0158174 A1*  6/2013   Wu .................. C08F 2/42
                                              252/182.17

FOREIGN PATENT DOCUMENTS

CN   107811889 A  *  3/2018
CN   108866103 A     11/2018
(Continued)

OTHER PUBLICATIONS

English translation of CN-108866103-A (Brruiser J) A soybean fermentation metabolite and its application, [Retrieved on Oct. 29, 2024] Retrieved from Espacenet <https://worldwide.espacenet.com/publicationDetails/>.*

(Continued)

*Primary Examiner* — Sue X Liu
*Assistant Examiner* — Dongxiu Zhang
(74) *Attorney, Agent, or Firm* — Birch, Stewart, Kolasch & Birch, LLP

(57) ABSTRACT

The present invention relates to a cosmetic composition comprising: palmitoylethanolamide; one or more of a pentanediol and a hexanediol; and a butanediol, and the cosmetic composition can allow palmitoylethanolamide to be sufficiently dissolved with the combination of the butanediol and one or more of the pentanediol and hexanediol, alleviate skin irritation caused by the solvent, and exhibit a skin soothing effect due to palmitoylethanolamide.

9 Claims, 2 Drawing Sheets

(56) References Cited

FOREIGN PATENT DOCUMENTS

| | | |
|---|---|---|
| CN | 110200875 B | 3/2022 |
| KR | 10-2021-0109456 A | 9/2021 |
| WO | WO2016/183134 A1 | 11/2016 |

OTHER PUBLICATIONS

English translation of CN-107811889-A (Huang Z. et al.) Mineral-oil-free warming harnd cream with heat sensitization, [Retrieved on Oct. 31, 2024] Retrieved from Espacenet <https://worldwide.espacenet.com/publication Details/>.*
"C1 Barrier Cream," Mintel, Feb. 29, 2016, 5 pages total.
"Retexturing Line Correcting Eye Cream," Mintel, Mar. 31, 2006, pp. 1-4.
Sirikudta et al., "Moisturizers for Patients with Atopic Dermatitis: An Overview", Journal of Allergy & Therapy, 2013, vol. 4. No. 4, p. 1-6.
Yuan et al., "N-palmitoylethanolamine and N-acetylethanolamine are effective in asteatotic eczema: results of a randomized, double-blind, controlled study in 60 patients", Clinical Interventions in Aging, Jul. 17, 2014, vol. 9, p. 1163-1169.

* cited by examiner

[FIG. 1]
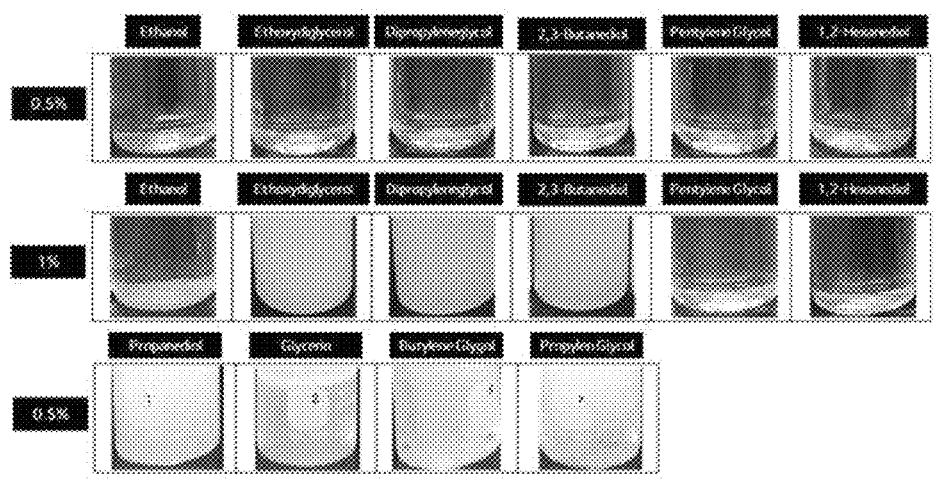
[FIG. 2]
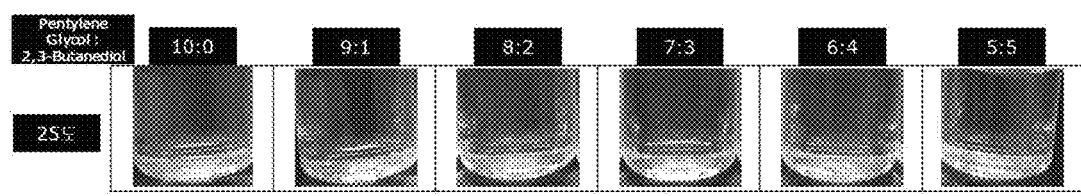
[FIG. 3]
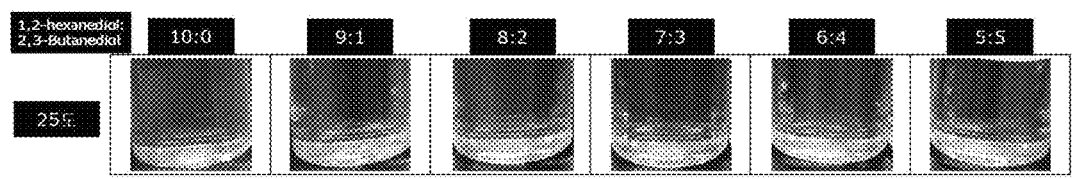

[FIG. 4]
(Comparative Example 4)
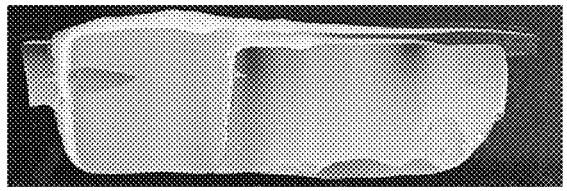
(Example 4)
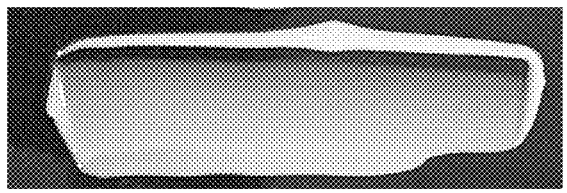
(Example 5)
[FIG. 5]
(Comparative Example 5)
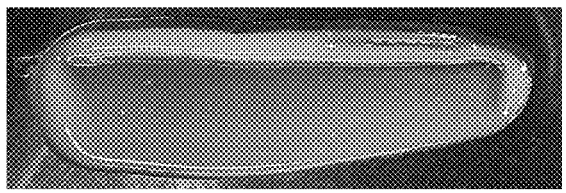
(Example 6)
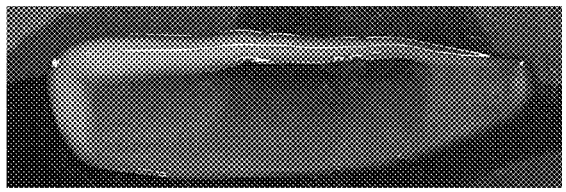
(Example 7)
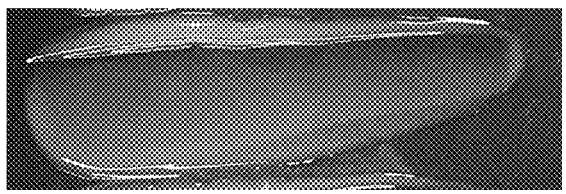

COSMETIC COMPOSITION COMPRISING PALMITOYLETHANOLAMIDE FOR SOOTHING EFFECT ON THE SKIN

CROSS-REFERENCE TO RELATED APPLICATION

This application claims priority to and the benefit of Korean Patent Application No. 2021-0185262, filed on Dec. 22, 2021, the disclosure of which is incorporated herein by reference in its entirety.

BACKGROUND

1. Field of the Invention

The present invention relates to a cosmetic composition comprising palmitoylethanolamide (PEA), and specifically, to a cosmetic composition comprising: palmitoylethanolamide; one or more of a pentanediol and a hexanediol; and a butanediol.

2. Discussion of Related Art

The chemical name of palmitoylethanolamide (PEA) is N-(2-hydroxyethyl)hexadecanamide. PEA is also called N-palmitoylethanolamine, palmitamide MEA, PMEA, or palmidrol and is an amide compound derived from C16 palmitic acid. According to the Personal Care Products Council (PCPC), an American cosmetic association, PEA is reported to have the function of "surfactants-foam boosters; viscosity increasing agents-aqueous," and the Korean cosmetic association also lists surfactants (foam boosters) and viscosity increasing agents (aqueous) as the mixing purposes of PEA.

PEA is known to indirectly activate cannabinoid (CB) receptors. As representative CB receptors, there are CBR1 and CBR2, and it is known that CBR1 is present mainly in the central nervous system, whereas CBR2 is present in the immune system. PEA is known to inhibit inflammation by participating in the expression of CBR2 among the CB receptors through PPAR-a. Patent Document 1 (U.S. Pat. No. 6,503,492 B2) confirmed that, when PEA was added to deodorant and antiperspirant formulations, histamine-induced itching was reduced, and an inflammatory index IL-6 was reduced. Also, in Patent Document 2 (U.S. Pat. No. 9,623,000 B2), PEA was added to hydrocortisone to treat inflammatory diseases. As described above, many related-art documents prove that PEA has a skin soothing effect, a pain-relieving effect (analgesic effect), an anti-inflammatory effect, and an immune-enhancing effect.

PEA is a white powder and has a very high melting point ranging from 93° C. to 98° C. The water solubility of PEA at 25° C. is 0.4431 mg/L and thus is classified as a substance that is insoluble in water based on the solubility classification standard. Also, due to the amide group in the chemical structure, PEA is not easily dissolved in medium-chain triglyceride oils (MCT oils) generally used in skincare products. In order to apply PEA to products, a heating process is essential. In the industry, compositions are prepared by heating an oil phase to 75° C. or more, then adding PEA, checking the dissolution condition (heating/dissolution/checking processes), and performing an emulsion process. Therefore, it is difficult to apply PEA to an o/w cream formulation or solubilized formulation prepared by a room-temperature process. The heating/dissolution/checking processes may degrade production efficiency during product production and deteriorate the working environment of producers. However, when PEA is directly added to water or a cosmetic formulation without a heating process, aggregation is promoted, and thus PEA precipitates at low temperature. Therefore, the heating/dissolution/checking processes cannot be omitted when considering the distribution process of products.

Meanwhile, organic solvents such as ethanol, dipropylene glycol, and the like, which are used to dissolve a solute, are known to cause irritation by weakening the skin barrier when an excessive amount is applied to the skin. Accordingly, when an excessive amount of the solvent is applied to sufficiently dissolve PEA, irritation caused by the solvent is also expected to increase.

Therefore, search for a suitable solvent that is capable of sufficiently dissolving PEA and that does not cause a problem such as skin irritation is required. The inventors of the present invention have found that the above problems are resolved by using a combination of specific solvents and thus completed the present invention.

RELATED-ART DOCUMENTS

Patent Documents (Patent Document 1) US Patent Publication No. 6503492 B2
(Patent Document 2) US Patent Publication No. 9623000 B2

SUMMARY OF THE INVENTION

The present invention is directed to providing a solvent capable of improving the solubility of palmitoylethanolamide.

The present invention is also directed to providing a composition for alleviating skin irritation caused by the solvent.

Therefore, the present invention is directed to providing a solvent which sufficiently dissolves palmitoylethanolamide and a composition which resolves a problem such as skin irritation caused by the solvent.

The present invention is also directed to providing a cosmetic composition that soothes skin by making it easier to apply palmitoylethanolamide, which is able to exhibit a skin soothing effect, to a cosmetic.

As a result of intensive research efforts to achieve the above objectives, the inventors of the present invention were able to select a pentanediol and a hexanediol as suitable solvents which are capable of dissolving palmitoylethanolamide. However, when an excessive amount of a pentanediol or a hexanediol is used, skin irritation occurs. Accordingly, the inventors have found that, when pentanediol and hexanediol contents are reduced by using these solvents in combination with a butanediol, palmitoylethanolamide can be sufficiently dissolved, the occurrence of skin irritation caused by pentanediol or hexanediol can be alleviated, and the skin soothing effect resulting from palmitoylethanolamide can be sufficiently exhibited.

Therefore, the present invention provides a cosmetic composition which comprises: palmitoylethanolamide; one or more of a pentanediol and a hexanediol; and a butanediol.

In addition, the present invention provides a cosmetic composition for skin soothing, which comprises the above ingredients.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which:

FIG. 1 is an image showing whether palmitoylethanolamide is dissolved in each solvent according to Experimental Example 1;

FIG. 2 is an image showing whether palmitoylethanolamide is dissolved in pentylene glycol and 2,3-butanediol according to Experimental Example 2;

FIG. 3 is an image showing whether palmitoylethanolamide is dissolved in 1,2-hexanediol and 2,3-butanediol according to Experimental Example 2;

FIG. 4 is an image showing whether palmitoylethanolamide is precipitated in a composition of Preparation Example 3 according to Experimental Example 4-1; and FIG. 5 is an image showing whether palmitoylethanolamide is precipitated in a composition of Preparation Example 4 according to Experimental Example 4-1.

DETAILED DESCRIPTION OF EXEMPLARY EMBODIMENTS

Hereinafter, the present invention will be described in detail.

The present invention provides a cosmetic composition comprising: palmitoylethanolamide; one or more of a pentanediol and a hexanediol; and a butanediol.

In the present invention, "palmitoylethanolamide" or "PEA" is represented by the following Chemical Formula 1 and has a structure in which a palmitoyl carboxylate group is amidated by the primary amine of ethanolamine.

[Chemical Formula 1]

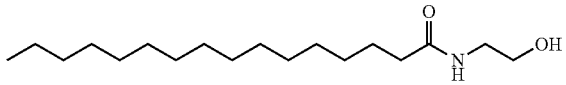

Palmitoylethanolamide is a CBR activator and is capable of reducing itching caused by histamine. Also, palmitoylethanolamide has a skin soothing effect, an anti-inflammatory effect, an antinociceptive effect, and an analgesic effect. Accordingly, palmitoylethanolamide may be used for pain alleviation in chronic pain management, management of abnormal inflammatory pain and/or immune response-induced pain, and the like.

Palmitoylethanolamide is insoluble in water at room temperature and is not dissolved in medium-chain triglyceride oils (MCT oils) at room temperature or even when heated to 50° C. Accordingly, in the present invention, one or more of a pentanediol and a hexanediol may be used as a solvent of palmitoylethanolamide to sufficiently dissolve palmitoylethanolamide. Specifically, pentanediols and hexanediols may reversibly dissolve palmitoylethanolamide even when stored for a long period of time.

In the present invention, the pentanediol is a compound in which two hydroxyl group substitutions are present in pentane, and the position of the hydroxyl group substitution is not particularly limited. Examples of the pentanediol comprise 1,1-pentanediol, 2,2-pentanediol, 3,3-pentanediol, 1,2-pentanediol, 1,3-pentanediol, 1,4-pentanediol, 1,5-pentanediol, 2,3-pentanediol, 2,4-pentanediol, and the like. Preferably, the pentanediol is pentylene glycol, which is 1,2-pentanediol.

In the present invention, the hexanediol is a compound in which two hydroxyl group substitutions are present in hexane, and the position of the hydroxyl group substitution is not particularly limited. Examples of the hexanediol comprise 1,1-hexanediol, 2,2-hexanediol, 3,3-hexanediol, 1,2-hexanediol, 1,3-hexanediol, 1,4-hexanediol, 1,5-hexanediol, 1,6-hexanediol, 2,3-hexanediol, 2,4-hexanediol, 2,5-hexanediol, 3,4-hexanediol, and the like. Preferably, the hexanediol is 1,2-hexanediol.

"Pentylene glycol" described as a preferred example of the pentanediol is an alcohol, which is able to be extracted from sugar cane, corn, or the like, and may help retain moisture and skin elasticity, and therefore it may also be used as a moisturizer and a skin conditioning agent in a cosmetic.

In addition, "1,2-hexanediol" described as a preferred example of the hexanediol has a skin moisturizing effect, an antimicrobial effect, and an antioxidant effect, and therefore it may have a stabilizing function to prevent oxidation of a cosmetic and may also be used as a moisturizer and a preservative.

In addition, some of the pentanediol and hexanediol selected as solvents of palmitoylethanolamide is substituted with a butanediol to reduce pentanediol and hexanediol contents, and thus skin irritation caused by pentanediol or hexanediol may be alleviated.

Although a "butanediol" is not capable of sufficiently dissolving palmitoylethanolamide by itself, a butanediol is capable of sufficiently dissolving palmitoylethanolamide by being used in combination with the pentanediol and hexanediol that serve as solvents and may alleviate skin irritation caused by the solvents.

In an embodiment of the present invention, the butanediol may be one or more selected from 1,1-butanediol, 2,2-butanediol, 1,2-butanediol, 1,4-butanediol, and 2,3-butanediol, with 2,3-butanediol being most preferred.

In an embodiment of the present invention, a weight ratio of the one or more of the pentanediol and hexanediol:the butanediol may be 9.5:0.5 to 4.5:5.5. Preferably, a weight ratio of the one or more of the pentanediol and hexanediol: the butanediol is 9.5:0.5 to 5.5:4.5 or 9.5:0.5 to 6.5:3.5.

Specifically, a weight ratio of pentanediol:butanediol may be 9.5:0.5 to 7.5:2.5, and a weight ratio of hexanediol: butanediol may be 9.5:0.5 to 5.5:4.5.

In an embodiment of the present invention, palmitoylethanolamide may be comprised in an amount of 0.001 to 3 wt % relative to the total weight of the cosmetic composition. For example, palmitoylethanolamide may be comprised in an amount of 0.001 to 2 wt %, 0.01 to 1 wt %, 0.01 to 0.1 wt %, or 0.01 to 0.07 wt %.

In an embodiment of the present invention, the one or more of the pentanediol and hexanediol may be comprised in an amount of 1 to 8 wt % relative to the total weight of the cosmetic composition. For example, the one or more of the pentanediol and hexanediol may be comprised in an amount of 2 to 7 wt %, 2.5 to 6 wt %, or 3 to 5 wt %.

In an embodiment of the present invention, the butanediol may be comprised in an amount of 0.1 to 5 wt % relative to the total weight of the cosmetic composition. For example, the butanediol may be comprised in an amount of 0.1 to 3 wt %, 0.1 to 2.5 wt %, 0.5 to 2.5 wt %, or 0.5 to 1.8 wt %. When the butanediol is comprised within the above-described range, palmitoylethanolamide can be sufficiently dissolved without being precipitated, and an effect of alleviating skin irritation can be exhibited.

In an embodiment of the present invention, the one or more of the pentanediol and hexanediol and the butanediol may be comprised in an amount of 50 to 250 parts by weight relative to 1 part by weight of palmitoylethanolamide. More specifically, the one or more of the pentanediol and hexanediol and the butanediol may be comprised in an amount of 80 to 120 parts by weight relative to 1 part by weight of palmitoylethanolamide. Since the one or more of the pentanediol and hexanediol and the butanediol serve as solvents that dissolve palmitoylethanolamide which is a solute, they need to be comprised in excessive amounts based on palmitoylethanolamide and may be comprised in the above amounts (parts by weight), but the present invention is not limited thereto.

The sum of weights of palmitoylethanolamide, one or more of the pentanediol and hexanediol, and the butanediol may be 1 to 10 wt % relative to the total weight of the composition. For example, the sum of weights may be 1 to 8 wt %, 1 to 7 wt %, 1 to 5 wt %, 2 to 8 wt %, or 3 to 6 wt %.

In an embodiment of the present invention, palmitoylethanolamide may be comprised in an amount of 0.2 to 10 wt % relative to the sum of weights of palmitoylethanolamide, one or more of the pentanediol and hexanediol, and the butanediol. For example, palmitoylethanolamide may be comprised in an amount of 0.5 to 8 wt %, 0.5 to 5 wt %, 0.5 to 2 wt %, or 0.5 to 1.5 wt % relative to the sum of weights of palmitoylethanolamide, one or more of the pentanediol and hexanediol, and the butanediol.

In an embodiment of the present invention, the one or more of the pentanediol and hexanediol may be comprised in an amount of 40 to 94.8 wt % relative to the sum of weights of palmitoylethanolamide, one or more of the pentanediol and hexanediol, and the butanediol. For example, the one or more of the pentanediol and hexanediol may be comprised in an amount of 50 to 94.8 wt %, 55 to 90 wt %, or 60 to 85 wt % relative to the sum of weights of palmitoylethanolamide, one or more of the pentanediol and hexanediol, and the butanediol.

In an embodiment of the present invention, the butanediol may be comprised in an amount of 5 to 40 wt % relative to the sum of weights of palmitoylethanolamide, one or more of the pentanediol and hexanediol, and the butanediol. For example, the butanediol may be comprised in an amount of 10 to 35 wt % or 15 to 35 wt % relative to the sum of weights of palmitoylethanolamide, one or more of the pentanediol and hexanediol, and the butanediol.

In the preparation of the cosmetic composition according to the present invention, a step of mixing palmitoylethanolamide, one or more of the pentanediol and hexanediol, and the butanediol and stirring the resultant to prepare a solid-phase or liquid-phase mixture may be comprised.

In the mixture preparation step, the mixture in which palmitoylethanolamide is sufficiently dissolved may be prepared by mixing palmitoylethanolamide with a mixture of the butanediol and one or more of the pentanediol and hexanediol and stirring the resultant.

Specifically, the mixture preparation step may comprise adding palmitoylethanolamide to a mixture of the butanediol and one or more of the pentanediol and hexanediol and then heating and stirring the resultant at 40 to 70° C.

The cosmetic composition of the present invention may further comprise active ingredients typically used in a cosmetic composition, other than the aforementioned active ingredients. For example, a typical adjuvant such as an antioxidant, a stabilizing agent, a solubilizer, a vitamin, a UV absorber, a preservative, a pH control agent, a colorant, a pigment, and a fragrance; a carrier; and the like may be comprised.

The cosmetic composition of the present invention may be prepared in any of formulations typically prepared in the art and may be, for example, formulated into a solution, a suspension, an emulsion, a paste, a gel, a cream, a lotion, a powder, a soap, a surfactant-containing cleanser, an oil, a powder foundation, an emulsion foundation, a wax foundation, a pack, a massage cream, a spray, or the like, but the present invention is not limited thereto. More specifically, the cosmetic composition may be prepared in a formulation which is a toner, a lotion, a soft lotion, a nutritional lotion, a nutritional cream, a massage cream, an essence, an eye cream, a cleansing cream, a cleansing foam, a cleansing water, a pack, a spray, or a powder.

The cosmetic composition according to the present invention may be a cosmetic composition for skin soothing. A skin soothing effect is exhibited by palmitoylethanolamide, and the skin soothing effect resulting from palmitoylethanolamide can be sufficiently exhibited even when palmitoylethanolamide is mixed with the pentanediol, hexanediol, and butanediol.

The cosmetic composition according to the present invention may be a cosmetic composition in which the solubility of palmitoylethanolamide is improved. When palmitoylethanolamide is mixed with the butanediol and one or more of the pentanediol and hexanediol, palmitoylethanolamide does not precipitate even when allowed to stand at room temperature for a long period of time, and thus improved solubility can be exhibited.

The present invention also provides an external preparation for the skin, which comprises the cosmetic composition according to the present invention. Examples of an external preparation for the skin comprise anything applied to the outside of the skin and may be a cosmetic, drug, and quasi-drug in various formulations.

The present invention also provides a method of improving the solubility of palmitoylethanolamide, which comprises mixing palmitoylethanolamide with a butanediol and one or more of a pentanediol and a hexanediol.

The present invention also provides a use of a butanediol and one or more of a pentanediol and a hexanediol in preparation of a composition in which the solubility of palmitoylethanolamide is improved.

The present invention also provides a method of soothing the skin, which comprises administering a composition comprising: palmitoylethanolamide; one or more of a pentanediol and a hexanediol; and a butanediol to the skin of a subject in need thereof.

The present invention also provides a use of palmitoylethanolamide, one or more of a pentanediol and a hexanediol, and a butanediol in preparation of a composition for skin soothing.

The composition for skin soothing may be a cosmetic composition for skin soothing.

Administration conditions such as route, subject, and dosage of the "administration" are not particularly limited, and conditions typically used in the administration of a cosmetic composition in the art may be used without limitation.

Each of the above-described ingredients comprised in the cosmetic composition according to the present invention may be comprised in the cosmetic composition of the present invention within a range that does not exceed the maximum usage amount specified in the "Cosmetic Safety and Technical Standards" or "Cosmetics Use and Permission" prescribed by the governments of Korea, China, the United States, and the like.

Hereinafter, the present invention will be described in detail with reference to the following experimental examples. However, it should be understood that the following experimental examples are given for the purpose of illustration only and are not intended to limit the scope of the present invention. Also, these experimental examples are provided for promoting understanding of the present invention only, and the scope of the present invention is not limited thereto.

EXAMPLES

Experimental Example 1. Selection of Solvent of Palmitoylethanolamide

The solubility of palmitoylethanolamide in each solvent was determined. Polyols representatively used as solvents of cosmetics were chosen, which were propanediol, glycerin, ethanol, 2,3-butanediol, pentylene glycol, dipropylene glycol, propylene glycol, butylene glycol, ethoxydiglycerol, and 1,2-hexanediol. 0.5 wt % palmitoylethanolamide and 1 wt % palmitoylethanolamide were each dissolved in the polyols. The resulting solution was allowed to stand at 25° C. for 24 hours, and then it was determined whether the polyols were capable of dissolving palmitoylethanolamide.

FIG. 1 is an image showing the solubility of 0.5 wt % and 1 wt % palmitoylethanolamide in each polyol, after they were allowed to stand at 25° C. for 24 hours.

As shown in FIG. 1, it can be confirmed that in the case of pentylene glycol and 1,2-hexanediol, solutions were transparent when allowed to stand at 25° C. for 24 hours, indicating good solubility, whereas the remaining polyol solutions appeared white, indicating precipitation. From the result, pentylene glycol and 1,2-hexanediol were selected as most preferred solvents for palmitoylethanolamide.

Experimental Example 2. Determination of Solubility of Palmitoylethanolamide According to Combined Use of Selected Solvents and 2,3-butanediol The solubility of palmitoylethanolamide according to combined use of the solvents selected in Experimental Example 1, pentylene glycol and 1,2-hexanediol, with 2,3-butanediol was determined.

Specifically, 1 wt % palmitoylethanolamide was dissolved in a solution in which pentylene glycol or 1,2-hexanediol was mixed with 2,3-butanediol at a specific ratio, and the resultant was allowed to stand at 25° C. for 4 weeks. Then, the solubility of palmitoylethanolamide was determined.

As shown in FIGS. 2 and 3, when pentylene glycol or 1,2-hexanediol was used in combination with 2,3-butanediol, 1 wt % palmitoylethanolamide was dissolved regardless of a weight ratio thereof.

Experimental Example 3. Evaluation of Primary Irritation on Human Skin

Preparation Example 1. Preparation of Composition Using Pentylene Glycol

Ingredients 2 to 4 were slowly added to and dispersed in Ingredient 1, and then the resultant was heated to 72° C. to prepare an aqueous phase. Ingredients 5 to 9 were mixed, melted by heating, and maintained at 72° C. to prepare an oil phase. The oil phase was slowly added to the aqueous phase while stirring the aqueous phase, and the resultant was homogeneously emulsified using a homo mixer and then cooled to 50° C. while stirring. Ingredient 10 dissolved in a small amount of Ingredient 1 was added thereto, and then Ingredients 11 to 13 were added and emulsified. The resultant was cooled to 28° C. while stirring to obtain compositions of Comparative Examples 1 and 2 and Example 1. The numbered ingredients and mixing mass % thereof are shown in the following Table 1.

TABLE 1

| | Mixing ingredients | Comparative Example 1 | Comparative Example 2 | Example 1 |
|---|---|---|---|---|
| 1 | Water | up to 100 | up to 100 | up to 100 |
| 2 | Trisodium EDTA | 0.02 | 0.02 | 0.02 |
| 3 | Acrylate/C10-30 alkyl acrylate crosspolymer | 0.08 | 0.08 | 0.08 |
| 4 | Ammonium acryloyldimethyltaurate/VP copolymer | 0.30 | 0.30 | 0.30 |
| 5 | Cetearyl alcohol | 0.50 | 0.50 | 0.50 |
| 6 | Ceteareth-6 olivate | 1.00 | 1.00 | 1.00 |
| 7 | Isostearyl isostearate | 6.00 | 6.00 | 6.00 |
| 8 | Squalene | 2.00 | 2.00 | 2.00 |
| 9 | Dimethicone | 1.00 | 1.00 | 1.00 |
| 10 | Tromethamine | 0.06 | 0.06 | 0.06 |
| 11 | Pentylene glycol | — | 4.95 | 3.96 |
| 12 | Palmitoylethanolamide | — | 0.05 | 0.05 |
| 13 | 2,3-Butanediol | — | — | 0.99 |
| Total | | 100 | 100 | 100 |

Experimental Example 3-1. Primary Irritation Evaluation Experiment

In order to evaluate the primary irritation appearing on the skin, an experiment was conducted on 20 healthy adult subjects having no skin diseases. An appropriate amount (about 25 µl) of the sample was applied onto each chamber of a patch test unit (IQ Ultra™), and then the patch test unit onto which the sample was applied was attached to the test site of the adult subjects. After 24 hours of attachment, the patch test unit was detached, and the skin condition was checked 2 hours after the detachment. The checking was performed once, irritancy was evaluated according to evaluation criteria shown in Table 2 and converted into a primary skin irritation index by the following Equation 1, and results thereof are shown in the following Table 3.

TABLE 2

| Irritancy (Score) | Evaluation criteria |
|---|---|
| 0 | no symptoms |
| 0.5 | only mild erythema |
| 1 | obvious erythema, tingling, and edema without blistering |
| 2 | obvious erythema, tingling, and edema with blistering |
| 3 | severe erythema and bulla |

Primary skin irritation index=ΣIrritancy of each subject/(Number of subjects tested×Number of readings)     [Equation 1]

TABLE 3

| | Irritation index |
|---|---|
| Comparative Example 1 | 0.08 |
| Comparative Example 2 | 0.08 |
| Example 1 | 0.00 |

In the case of Example 1 comprising pentylene glycol and 2,3-butanediol, there was no subject with a skin irritant reaction, and the irritation index was 0. On the other hand, in the case of Comparative Example 1, which did not comprise any of palmitoylethanolamide, pentylene glycol, and 2,3-butanediol, and Comparative Example 2, which comprised palmitoylethanolamide and pentylene glycol but did not comprise 2,3-butanediol, 3 of 20 subjects had a skin irritant reaction accompanied with mild erythema, and both irritation indices were 0.08.

Therefore, it can be concluded that skin irritation can be alleviated by combining palmitoylethanolamide and pentylene glycol with 2,3-butanediol.

Preparation Example 2. Preparation of Composition Using 1,2-Hexanediol

Ingredients 2 to 4 were slowly added to and dispersed in Ingredient 1, and then the resultant was heated to 72° C. to prepare an aqueous phase. Ingredients 5 to 9 were mixed, melted by heating, and maintained at 72° C. to prepare an oil phase. The oil phase was slowly added to the aqueous phase while stirring the aqueous phase, and the resultant was homogeneously emulsified using a homo mixer and then cooled to 50° C. while stirring. Ingredient 10 dissolved in a small amount of Ingredient 1 was added thereto, and then Ingredients 11 to 13 were added and emulsified. The resultant was cooled to 28° C. while stirring to obtain compositions of Comparative Example 3 and Examples 2 and 3. The numbered ingredients and mixing mass % thereof are shown in the following Table 4.

TABLE 4

| | Mixing ingredients | Comparative Example 3 | Example 2 | Example 3 |
|---|---|---|---|---|
| 1 | Water | up to 100 | up to 100 | up to 100 |
| 2 | Trisodium EDTA | 0.02 | 0.02 | 0.02 |
| 3 | Acrylate/C10-30 alkyl acrylate crosspolymer | 0.08 | 0.08 | 0.08 |
| 4 | Ammonium acryloyldimethyltaurate/VP copolymer | 0.30 | 0.30 | 0.30 |
| 5 | Cetearyl alcohol | 0.50 | 0.50 | 0.50 |
| 6 | Ceteareth-6 olivate | 1.00 | 1.00 | 1.00 |
| 7 | Isostearyl isostearate | 6.00 | 6.00 | 6.00 |
| 8 | Squalene | 2.00 | 2.00 | 2.00 |
| 9 | Dimethicone | 1.00 | 1.00 | 1.00 |
| 10 | Tromethamine | 0.06 | 0.06 | 0.06 |
| 11 | 1,2-Hexanediol | 4.95 | 3.96 | 3.47 |
| 12 | Palmitoylethanolamide | 0.05 | 0.05 | 0.05 |
| 13 | 2,3-Butanediol | — | 0.99 | 1.48 |
| | Total | 100 | 100 | 100 |

Experimental Example 3-2. Primary Irritation Evaluation Experiment

A primary irritation evaluation experiment was conducted in the same manner as in Experimental Example 3-1, and the skin irritation index was calculated, which is shown in the following Table 5.

TABLE 5

| | Irritation index |
|---|---|
| Comparative Example 3 | 0.2 |
| Example 2 | 0.08 |
| Example 3 | 0.05 |

In the case of Examples 2 and 3 comprising 1,2-hexanediol and 2,3-butanediol, 3 and 2 of 20 subjects had mild erythema, and irritation indices were 0.08 and 0.05, respectively. On the other hand, in the case of Comparative Example 3, which did not comprise 2,3-butanediol, 6 of 20 subjects had an irritant reaction accompanied with mild erythema, 1 subject had an irritant reaction accompanied with obvious erythema, and a high irritation index of 0.2 was exhibited.

Therefore, it can be concluded that skin irritation can be alleviated by combining palmitoylethanolamide and 1,2-hexanediol with 2,3-butanediol.

Experimental Example 4. Evaluation of Solubility and Skin Soothing Effect of Composition In this experiment, final compositions comprising palmitoylethanolamide were prepared, and the dissolution of palmitoylethanolamide in the composition and the skin soothing effect of the composition were determined.

Preparation Example 3. Preparation of Compositions of Comparative Example 4 and Examples 4 and 5

Ingredients 2 to 4 were slowly added to and dispersed in Ingredient 1, and then the resultant was heated to 72° C. to prepare an aqueous phase. Ingredients 5 to 9 were mixed, melted by heating, and maintained at 72° C. to prepare an oil phase. The oil phase was slowly added to the aqueous phase while stirring the aqueous phase, and the resultant was homogeneously emulsified using a homo mixer and then cooled to 50° C. while stirring. Ingredient 10 dissolved in a small amount of Ingredient 1 was added thereto, and then Ingredients 11 to 13 were added and emulsified. The resultant was cooled to 28° C. while stirring to obtain compositions of Comparative Example 4 and Examples 4 and 5. The numbered ingredients and mixing mass % thereof are shown in the following Table 6.

TABLE 6

| | Mixing ingredients | Comparative Example 4 | Example 4 | Example 5 |
|---|---|---|---|---|
| 1 | Water | up to 100 | up to 100 | up to 100 |
| 2 | Trisodium EDTA | 0.02 | 0.02 | 0.02 |
| 3 | Acrylate/C10-30 alkyl acrylate crosspolymer | 0.08 | 0.08 | 0.08 |
| 4 | Ammonium acryloyldimethyltaurate/VP copolymer | 0.3 | 0.3 | 0.3 |
| 5 | Cetearyl alcohol | 0.5 | 0.5 | 0.5 |
| 6 | Ceteareth-6 olivate | 1 | 1 | 1 |
| 7 | Isostearyl isostearate | 6 | 6 | 6 |
| 8 | Squalene | 2 | 2 | 2 |

TABLE 6-continued

| | Mixing ingredients | Comparative Example 4 | Example 4 | Example 5 |
|---|---|---|---|---|
| 9 | Dimethicone | 1 | 1 | 1 |
| 10 | Tromethamine | 0.06 | 0.06 | 0.06 |
| 11 | Pentylene glycol | — | 5.54 | 3.47 |
| 12 | Palmitoylethanolamide | 0.07 | 0.07 | 0.07 |
| 13 | 2,3-Butanediol | — | 1.39 | 3.46 |
| | Total | 100 | 100 | 100 |

Preparation Example 4. Preparation of Compositions of Comparative Example 5 and Examples 6 and 7

Ingredients 2 and 3 were slowly added to and dispersed in Ingredient 1, and then the resultant was heated to 60° C. to prepare an aqueous phase. Ingredients 4 to 7 were mixed, melted by heating, and maintained at 60° C. to prepare an oil phase. The oil phase was slowly added to the aqueous phase while stirring the aqueous phase, and the resultant was homogeneously emulsified using a homo mixer and then cooled to 50° C. while stirring. Ingredient 8 dissolved in a small amount of Ingredient 1 was added thereto, and then Ingredients 9 to 11 were added and emulsified. The resultant was cooled to 28° C. while stirring to obtain compositions of Comparative Example 5 and Examples 6 and 7. The numbered ingredients and mixing mass % thereof are shown in the following Table 7.

TABLE 7

| | Mixing ingredients | Comparative Example 5 | Example 6 | Example 7 |
|---|---|---|---|---|
| 1 | Water | up to 100 | up to 100 | up to 100 |
| 2 | Trisodium EDTA | 0.02 | 0.02 | 0.02 |
| 3 | Acrylate/C10-30 alkyl acrylate crosspolymer | 0.2 | 0.2 | 0.2 |
| 4 | Propanediol | 6 | 6 | 6 |
| 5 | Denatured alcohol | 3 | 3 | 3 |
| 6 | Dimethicone | 3 | 3 | 3 |
| 7 | Cetearyl alcohol | 0.5 | 0.5 | 0.5 |
| 8 | Tromethamine | 0.2 | 0.2 | 0.2 |
| 9 | Pentylene glycol | — | 5.54 | 3.47 |
| 10 | Palmitoylethanolamide | 0.07 | 0.07 | 0.07 |
| 11 | 2,3-Butanediol | — | 1.39 | 3.46 |
| | Total | 100 | 100 | 100 |

Experimental Example 4-1. Determination of Solubility of Palmitoylethanolamide in Composition Whether palmitoylethanolamide was precipitated in two types of compositions according to Preparation Examples 3 and 4 was determined. A small amount of the composition was thinly spread onto a transparent glass plate using a spatula, and then whether palmitoylethanolamide was precipitated was determined.

As shown in FIGS. 4 and 5, in the two types of compositions, Comparative Examples 4 and 5, which did not comprise pentylene glycol and 2,3-butanediol, showed precipitation, whereas Examples 4 to 7, which comprised pentylene glycol and 2,3-butanediol, did not show precipitation, which indicates that the solubility of palmitoylethanolamide was improved.

Therefore, it can be concluded that the solubility of palmitoylethanolamide can be improved by combining pentylene glycol and 2,3-butanediol regardless of the types and amounts of the remaining ingredients constituting the composition.

Experimental Example 4-2. Evaluation of Skin Soothing Effect of Compositions of Comparative Example 1 and Example 4

The skin soothing effects of the composition of Comparative Example 1 prepared according to Preparation Example 1 and the composition of Example 4 prepared according to Preparation Example 3 were evaluated.

A polyester tape having a diameter of 22 mm was attached to the skin below the elbow and constant pressure was applied for 5 seconds. Then the tape was slowly detached while the end of the tape was held. This process was repeated 10 times to induce skin irritation, and the composition was applied immediately after skin irritation was induced. In order to determine the level of skin soothing effect, the degree of erythema before and after application of the composition was measured using a colorimeter (skin chromaticity, a* (green~red)), and colorimeter measurement values and conversion values thereof are shown in Tables 8 and 9.

TABLE 8

| Measurement value | Before application Immediately after irritation | After application | | | |
|---|---|---|---|---|---|
| | | 10 minutes | 2 hours | 3 hours | 4 hours |
| Comparative Example 1 | 9.48 | 8.24 | 7.63 | 7.48 | 5.56 |
| Example 4 | 11.63 | 9.91 | 7.54 | 6.86 | 5.48 |

TABLE 9

| Conversion value (%) | Before application Immediately after irritation | After application | | | |
|---|---|---|---|---|---|
| | | 10 minutes | 2 hours | 3 hours | 4 hours |
| Comparative Example 1 | 100.00 | 86.88 | 80.49 | 78.94 | 58.68 |
| Example 4 | 100.00 | 85.21 | 64.85 | 59.03 | 47.10 |

It can be seen that, as compared to Comparative Example 1, which did not comprise palmitoylethanolamide, pentylene glycol, and 2,3-butanediol, Example 4, which comprised all of palmitoylethanolamide, pentylene glycol, and 2,3-butanediol showed relatively alleviated erythema 2 hours after application, and the skin was soothed.

The present invention can provide a suitable solvent that is capable of dissolving palmitoylethanolamide whose solubility is extremely low, and the solvent can stably dissolve palmitoylethanolamide even when stored for a long period of time. Accordingly, a process can be simplified in preparation of a cosmetic comprising palmitoylethanolamide.

In addition, since the solvent is used in combination with a butanediol, skin irritation caused by the solvent can be alleviated, and an inherent skin soothing characteristic of palmitoylethanolamide can be exhibited.

That is, the present invention can provide a solvent which is capable of sufficiently dissolving palmitoylethanolamide, alleviate skin irritation caused by the solvent by using the solvent in combination with a butanediol, and exhibit a skin soothing effect resulting from palmitoylethanolamide.

What is claimed is:

1. A cosmetic composition comprising:
palmitoylethanolamide (PEA);
one or more of a pentanediol and a hexanediol; and
a butanediol,
wherein the pentanediol is pentylene glycol, the hexanediol is 1,2-hexanediol, and the butanediol is 2,3-butanediol,
wherein the palmitoylethanolamide is included in an amount of 0.001 to 3 wt % relative to the total weight of the cosmetic composition.

2. The cosmetic composition of claim 1, wherein a weight ratio of the one or more of the pentanediol and hexanediol: the butanediol is 9.5:0.5 to 4.5:5.5.

3. The cosmetic composition of claim 1, wherein the butanediol is comprised in an amount of 0.1 to 5 wt % relative to the total weight of the cosmetic composition.

4. The cosmetic composition of claim 1, wherein the one or more of the pentanediol and hexanediol and the butanediol are comprised in an amount of 50 to 250 parts by weight relative to 1 part by weight of the palmitoylethanolamide.

5. The cosmetic composition of claim 1, wherein the sum of weights of the palmitoylethanolamide, one or more of the pentanediol and hexanediol, and the butanediol is 1 to 10 wt % relative to the total weight of the composition.

6. The cosmetic composition of claim 1, wherein the composition is for skin soothing.

7. An external preparation for skin, comprising the cosmetic composition according to claim 1.

8. A method of improving the solubility of palmitoylethanolamide, comprising mixing palmitoylethanolamide with a butanediol, a pentanediol and a hexanediol, wherein the butanediol is 2,3-butanediol, the pentanediol is pentylene glycol, and the hexanediol is 1,2-hexanediol.

9. A method of soothing the skin, comprising administering a composition according to claim 1 to the skin of a subject in need thereof.

* * * * *